United States Patent
Swoish et al.

(10) Patent No.: US 10,716,592 B2
(45) Date of Patent: Jul. 21, 2020

(54) SCALPEL BLADE LOADER

(71) Applicant: Aspen Surgical Products, Inc., Caledonia, MI (US)

(72) Inventors: Murray Swoish, Batesville, IN (US); Alexander Boelkins, Grand Rapids, MI (US)

(73) Assignee: Aspen Surgical Products Inc., Caledonia, MI (US)

( * ) Notice: Subject to any disclaimer, the term of this patent is extended or adjusted under 35 U.S.C. 154(b) by 99 days.

(21) Appl. No.: 15/695,250

(22) Filed: Sep. 5, 2017

(65) Prior Publication Data

US 2019/0069919 A1   Mar. 7, 2019

(51) Int. Cl.
| | |
|---|---|
| *A61B 17/3213* | (2006.01) |
| *A61B 17/3215* | (2006.01) |
| *B25G 3/02* | (2006.01) |
| *B26B 5/00* | (2006.01) |
| *A61B 17/3211* | (2006.01) |
| *B25G 1/10* | (2006.01) |

(52) U.S. Cl.
CPC ...... *A61B 17/3213* (2013.01); *A61B 17/3215* (2013.01); *B25G 1/102* (2013.01); *B25G 3/02* (2013.01); *B26B 5/00* (2013.01); *A61B 2017/32116* (2013.01); *A61B 2560/02* (2013.01); *A61B 2560/04* (2013.01)

(58) Field of Classification Search
CPC ............... A61B 17/32; A61B 17/3215; A61B 2017/32113; A61B 2017/32116; A61B 17/3213; B65D 82/08; B65D 82/0835; B25G 1/102; B25G 3/02; B25G 3/10; B25G 3/32; B25B 5/00

USPC ........................................................ 29/281.6
See application file for complete search history.

(56) References Cited

U.S. PATENT DOCUMENTS

| | | |
|---|---|---|
| 2,581,332 A | 1/1952 | Testi |
| 2,636,596 A | 4/1953 | Testi |
| 3,244,317 A | 4/1966 | Raybin |
| 3,626,592 A | 12/1971 | La Cas et al. |
| 4,106,620 A | 8/1978 | Brimmer et al. |
| 4,123,840 A | 11/1978 | Rumer, Jr. |
| 4,137,631 A | 2/1979 | Pickett et al. |
| 4,157,758 A | 6/1979 | Kozlowski, Jr. |
| 4,180,162 A | 12/1979 | Magney |
| 4,275,735 A | 6/1981 | Chutter |
| 4,746,016 A | 5/1988 | Pollak et al. |
| 4,972,968 A | 11/1990 | Iten |

(Continued)

FOREIGN PATENT DOCUMENTS

DE   102009007292 A1   7/2010

*Primary Examiner* — Tyrone V Hall, Jr.
*Assistant Examiner* — Abbie E Quann
(74) *Attorney, Agent, or Firm* — Price Heneveld LLP

(57) ABSTRACT

A blade loader is provided herein. The blade loader includes a housing defining a cavity and an insertion opening at one end portion of the cavity. The cavity is configured to accept a blade therein. The housing includes first and second sections. First and second sidewalls extend from the respective first and second sections. The first sidewall is disposed outside the second sidewall. A support extends from the housing and into the cavity configured to interact with an aperture defined by the blade. A rib structure extends into the cavity and defines a channel and a press portion. The press portion is configured to contact a portion of the blade.

19 Claims, 15 Drawing Sheets

(56) References Cited

U.S. PATENT DOCUMENTS

| | | | |
|---|---|---|---|
| 4,998,334 A | * | 3/1991 | Pemberton ......... A61B 17/3217 29/239 |
| 5,251,783 A | | 10/1993 | Gringer |
| 5,272,812 A | | 12/1993 | Doucette |
| 5,275,606 A | | 1/1994 | Abidin et al. |
| 5,361,902 A | | 11/1994 | Abidin et al. |
| 5,363,958 A | * | 11/1994 | Horan ................ A61B 17/3215 206/356 |
| 5,411,512 A | | 5/1995 | Abidin et al. |
| 5,430,942 A | | 7/1995 | Doucette |
| 5,433,321 A | | 7/1995 | Abidin et al. |
| 5,528,811 A | | 6/1996 | Abidin et al. |
| 5,657,541 A | | 8/1997 | Hickok et al. |
| 5,662,221 A | | 9/1997 | Abidin et al. |
| 5,706,942 A | | 1/1998 | Vila et al. |
| 5,727,682 A | * | 3/1998 | Abidin ............... A61B 17/3215 206/354 |
| 5,875,532 A | | 3/1999 | Musgrave et al. |
| 5,938,027 A | | 8/1999 | Soroff et al. |
| 6,216,868 B1 | | 4/2001 | Rastegar et al. |
| 6,605,100 B1 | | 8/2003 | Shan et al. |
| 7,036,660 B1 | | 5/2006 | Abidin et al. |
| 7,155,795 B2 | | 1/2007 | Abidin et al. |
| 7,354,447 B2 | | 4/2008 | Shelton, IV et al. |
| 7,815,046 B2 | | 10/2010 | Sansoucy et al. |
| 7,857,824 B2 | | 12/2010 | Kiehne |
| 8,113,349 B2 | | 2/2012 | Sansoucy et al. |
| 8,757,378 B2 | | 6/2014 | Cote et al. |
| 8,931,181 B2 | | 1/2015 | Milton et al. |
| 8,931,636 B2 | | 1/2015 | Kierce et al. |
| 9,101,388 B2 | | 8/2015 | Yi et al. |
| 9,113,946 B2 | | 8/2015 | Hajgato et al. |
| 2002/0188309 A1 | | 12/2002 | Adelman et al. |
| 2009/0259241 A1 | | 10/2009 | Nakamura |
| 2011/0166555 A1 | | 7/2011 | Zhou et al. |

* cited by examiner

SCALPEL BLADE LOADER

TECHNOLOGICAL FIELD

The present disclosure generally relates to a container for medical blades. More specifically, a container for maintaining a medical blade prior to attachment to a scalpel handle.

BACKGROUND

Accidental cuts or punctures may occur due to blade instruments. In particular, scalpels may include a reusable handle that can be assembled with a disposable blade. Such handles may not include any protection from contact with the blade when assembled thereto and may present an additional opportunity for injury during attachment of the blade. Accordingly, further advances in protection from injury due to inadvertent contact with scalpel blades, including during attachment of the blades, are desired.

SUMMARY

According to one aspect of the disclosure, a blade loader is disclosed. The blade loader includes a housing defining a cavity and an insertion opening at one end portion of the cavity. The cavity is configured to accept a blade therein. The housing includes a first section coupled to a second section. First and second sidewalls extend from the respective first and second sections. The first sidewall is disposed outwardly of the second sidewall. A support extends from the housing and into the cavity and is configured to interact with an aperture in the blade. A rib structure extends into the cavity and defines a channel and a press portion. The press portion is configured to contact a portion of the blade.

According to another aspect of the disclosure, a blade loader is disclosed. The blade loader includes a housing having first and second sections defining a cavity therebetween and an insertion opening at one end portion of the cavity. The cavity is configured to accept a blade therein. The first section defines a slot proximate the insertion opening. A support extends from the second section and into the cavity and is configured to interact with an aperture defined by the blade. A portion of the support is disposed forwardly of an end portion of the slot.

According to yet another aspect of the disclosure, a blade loader is disclosed. The blade loader includes a housing defining a cavity and an insertion opening at one end portion of the cavity. The housing includes a first section coupled to a second section. A blade is disposed within the cavity. A rib structure extends into the cavity and is configured to contact a portion of the blade. First and second pivotable protrusions extend from the housing and into the cavity and are configured to interact with an aperture in the blade.

These and other features, advantages, and objects of the present device will be further understood and appreciated by those skilled in the art upon studying the following specification, claims, and appended drawings.

DETAILED DESCRIPTION OF EMBODIMENTS

Figure 1:
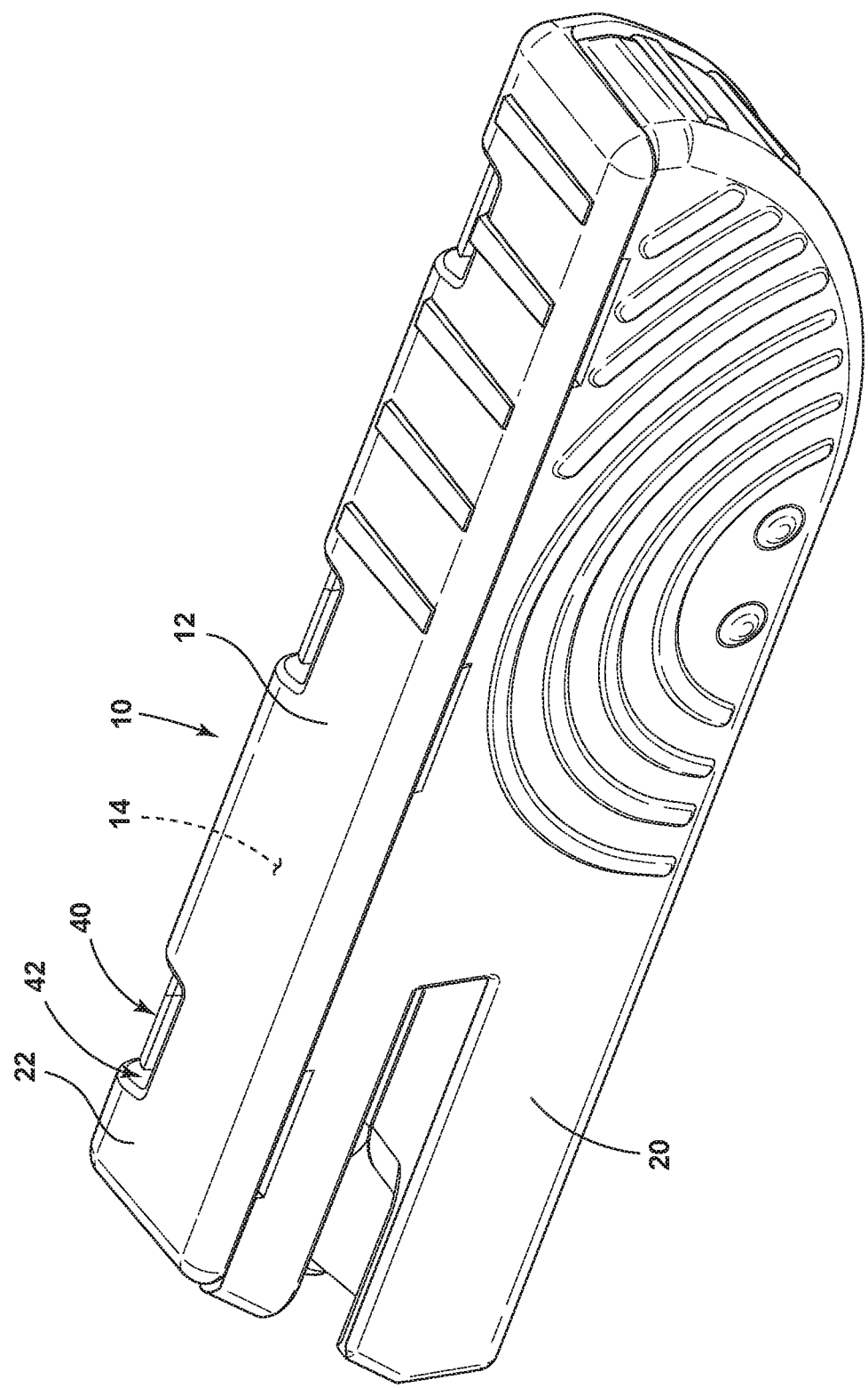
FIG. 1 is a top perspective view of a blade loader of the present disclosure, according to some examples.

For purposes of description herein, the terms "upper," "lower," "right," "left," "rear," "front," "vertical," "horizontal," and derivatives thereof shall relate to the disclosure as oriented in FIG. 1. However, it is to be understood that the invention may assume various alternative orientations, except where expressly specified to the contrary. It is also to be understood that the specific devices and processes illustrated in the attached drawings, and described in the following specification are simply exemplary embodiments of the inventive concepts defined in the appended claims. Hence, specific dimensions and other physical characteristics relating to the embodiments disclosed herein are not to be considered as limiting, unless the claims expressly state otherwise.

As required, detailed embodiments of the present disclosure are disclosed herein. However, it is to be understood that the disclosed embodiments are merely exemplary of the disclosure that may be embodied in various and alternative forms. The figures are not necessarily to a detailed design and some schematics may be exaggerated or minimized to show function overview. Therefore, specific structural and functional details disclosed herein are not to be interpreted as limiting, but merely as a representative basis for teaching one skilled in the art to variously employ the present disclosure.

As used herein, the term "and/or," when used in a list of two or more items, means that any one of the listed items can be employed by itself, or any combination of two or more of the listed items can be employed. For example, if a composition is described as containing components A, B, and/or C, the composition can contain A alone; B alone; C alone; A and B in combination; A and C in combination; B and C in combination; or A, B, and C in combination.

Referring to FIGS. 1-18, reference numeral 10 generally designates a blade loader that includes a housing 12 defining a cavity 14 and an insertion opening 16 at one end portion of the cavity 14. The cavity 14 is configured to accept a blade 18 therein. The housing 12 includes first and second sections 20, 22. A support 24 extends from the housing 12 and into the cavity 14 and is configured to interact with an aperture 26 in the blade 18. A first rib structure 28 extends into the cavity 14 and defines a channel 30 and a press portion 32. The press portion 32 is configured to maintain the blade 18 in a desired position. The housing 12 further includes first and second sidewalls 34, 36 extending from the respective first and second sections 20, 22. The first sidewall 34 disposed outside the second sidewall 36.

Figure 2:
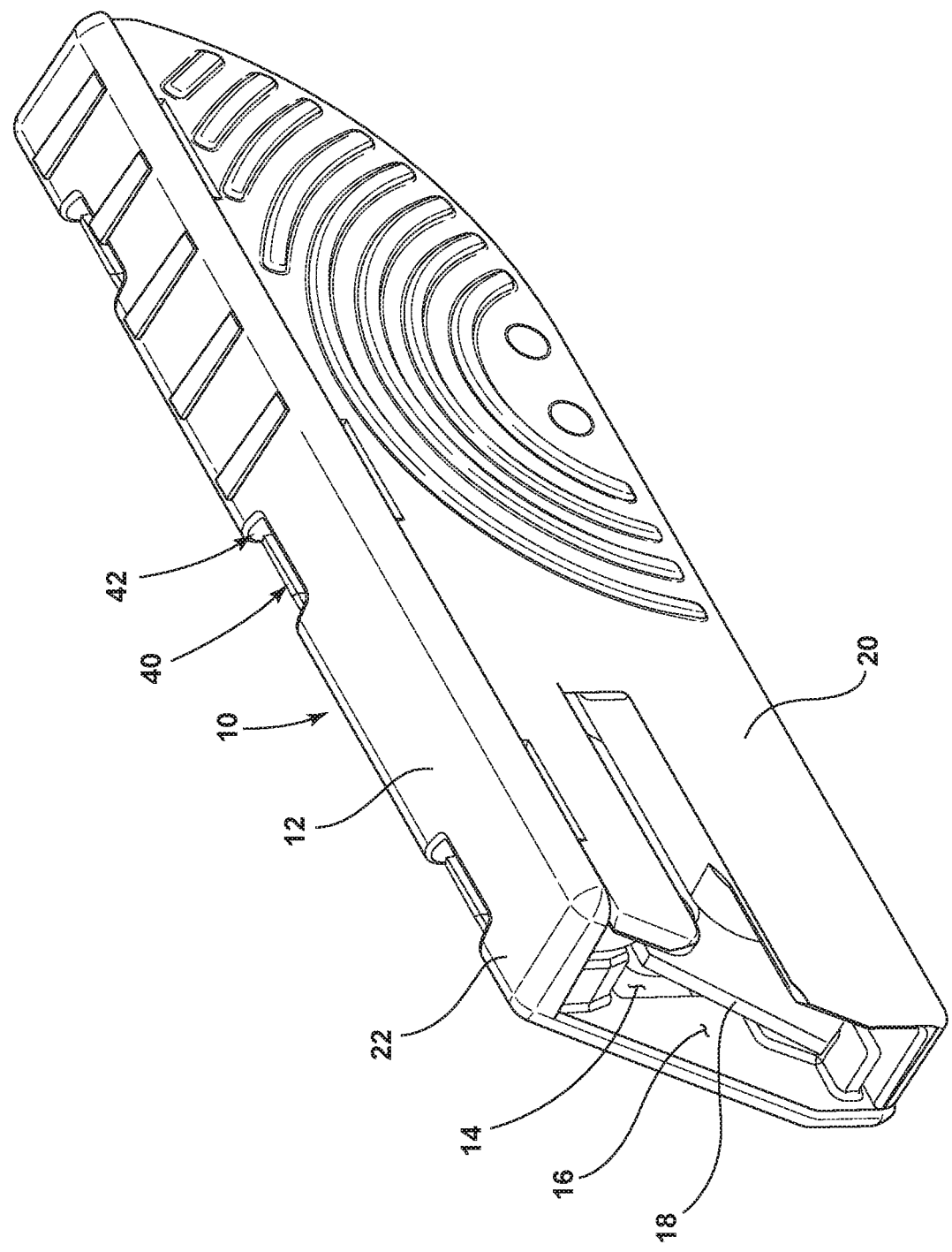
FIG. 2 is a top perspective view of the blade loader with a blade disposed therein, according to some examples.
Figure 4:
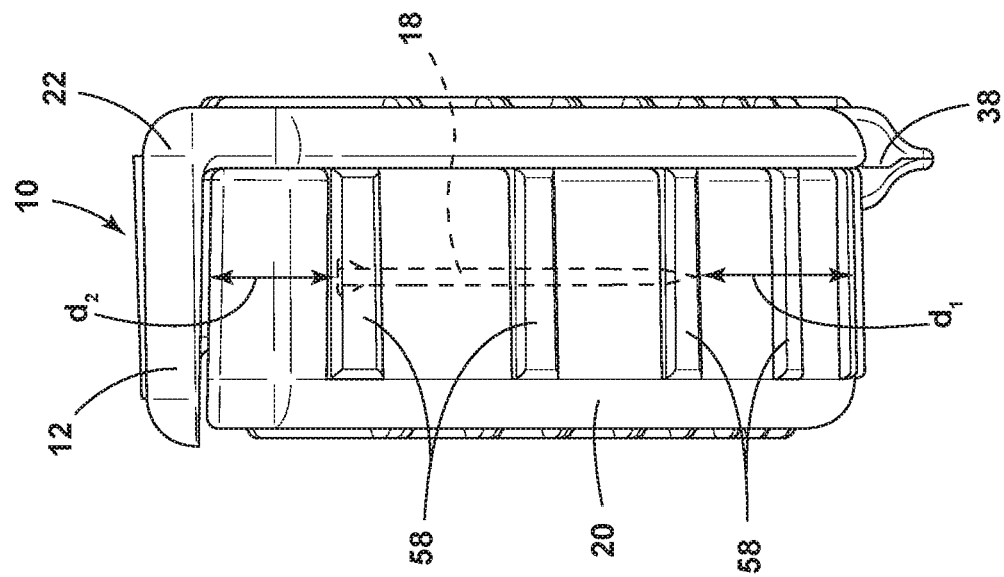
FIG. 4 is a front elevational view of the blade loader with a blade disposed therein shown in phantom, according to some examples.

Referring now to FIGS. 1 and 2, the blade loader 10 includes the housing 12. The housing 12 defines the first and second sections 20, 22 that may be coupled through a hinge 38 (FIG. 4). An attachment structure 40 may be disposed on the first section 20 and is operably coupled to an attachment region 42 on the second section 22. Once the first section 20 is attached to the second section 22, the cavity 14 is defined between the first and second sections 20, 22. It will be appreciated that the attachment structure 40 may be disposed on the second section 22 and the attachment region 42 may be disposed on the first section 20 without departing from the scope of the present disclosure.

Referring still to FIGS. 1 and 2, the surgical blade 18 may be retained within the cavity 14 and may be transported while it is retained within the blade loader 10. To retain the blade 18, the blade loader 10 may include a support 24 (FIG. 5) that interacts with the blade 18 to retain the blade 18 in a desired position. Additionally, or alternatively, one or more press portions 32 may be defined by the housing 12 that compressively maintain the blade 18 therein. It will be appreciated that the cavity 14 is generally configured to receive and secure blades 18 of varying sizes.

With further reference to FIGS. 1 and 2, the housing 12 may be fabricated from a molded polymer, such as homopolymer or copolymer polypropylene. It will be appreciated, however, that any practicable material may be used. Additionally, the housing 12 may be transparent, translucent, or opaque in various portions thereof. In transparent and/or translucent examples, a user of the blade loader 10 may be able to view the style of blade 18 disposed within the cavity 14 prior to attachment of the blade 18 to a scalpel handle 48.

Figure 3:
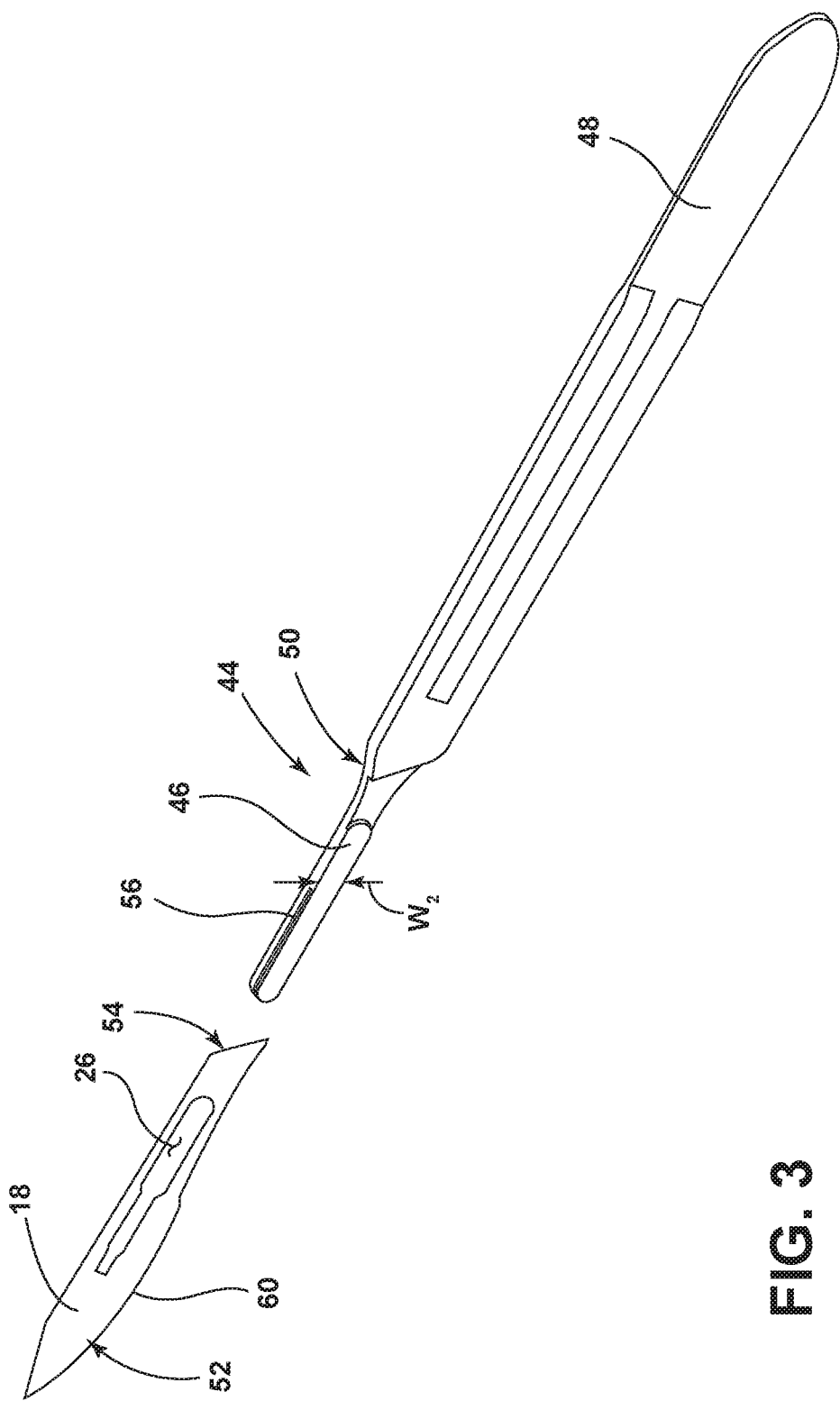
FIG. 3 is a top perspective view of a scalpel with a blade disengaged from a scalpel handle, according to some examples.

Referring to FIG. 3, a scalpel 44 is exemplarily illustrated and operably couplable to the removable blade 18. The blade 18 is disposed on a tang 46 that extends from a handle 48. The handle 48 is provided with a forward shoulder portion 50, which gradually narrows in width into the forwardly extending tang 46. The blade 18 includes a proximal cutting portion 52 and a distal heel portion 54. The proximal cutting portion 52 has a sharpened, cutting edge 60. In order to mount the blade 18 on the handle 48, the aperture 26 defined by the blade 18 is inserted into grooves 56 on the tang 46. The blade 18 is then slid towards the handle 48 and within the grooves 56. In this way, the blade 18 is locked onto the tang 46 and securely held in a desired position. It will be appreciated that the blade 18 may be any type of blade known in the art, including, but not limited to, stainless steel and carbon blades. Moreover, the blade loader 10 may accept a rib back, a non-rib back, or any other type of sharp therein without departing from the scope of the present disclosure.

Figure 5:
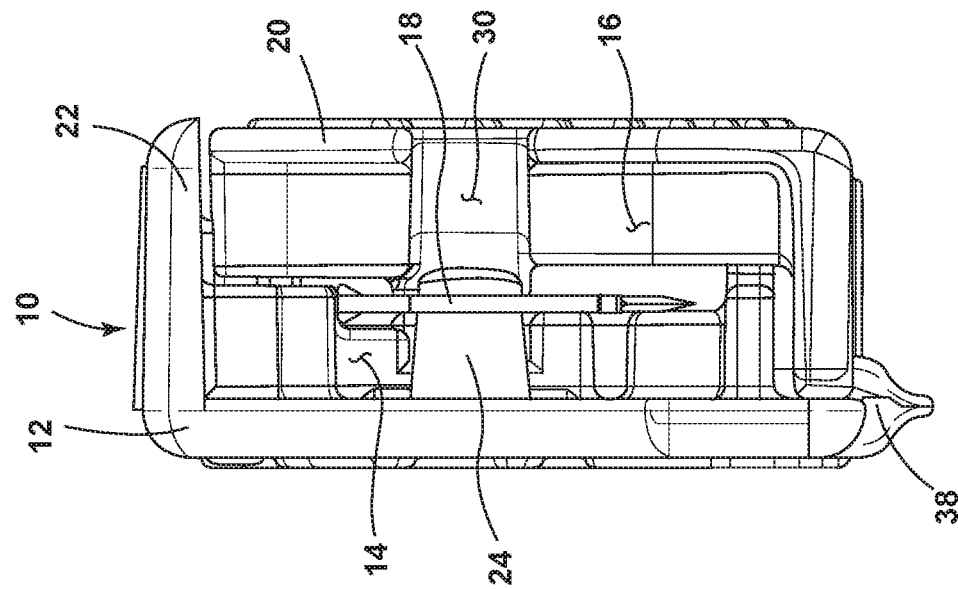
FIG. 5 is a rear elevational view of the blade loader with the blade disposed therein, according to some examples.

Referring to FIGS. 4 and 5, the first and second sections 20, 22 may be hingedly, or operably, coupled to one another. The hinge 38 is a flexible hinge that may be integrally formed within the housing 12 to separate the first section 20 from the second section 22. In some examples, the hinge 38 is a flexible living hinge (e.g., flexure bearing) and may be made from the same material as other portions of the housing 12. In some examples, the first and second sections 20, 22 may be otherwise attached to one another by any method known in the art. Moreover, in some examples, the housing 12 may be configured as a single component. In alternate examples, an additional component may be added to the assembly to form the hinge 38. The additional component may be any type of hinge 38 known in the art.

Referring to FIG. 4, the first section 20 of the housing 12 may include one or more ridges 58 thereon. The ridges 58 may increase a user's ability to grip the housing 12 while inserting a scalpel handle 48 into the housing 12 for attaching the blade 18 to the scalpel handle 48. The one or more ridges 58 may extend from the housing 12 and may be integrally formed therewith. Additionally, the ridges 58 may assist during use of the blade loader 10 while a user is wearing wet or dry gloves.

Figure 12:
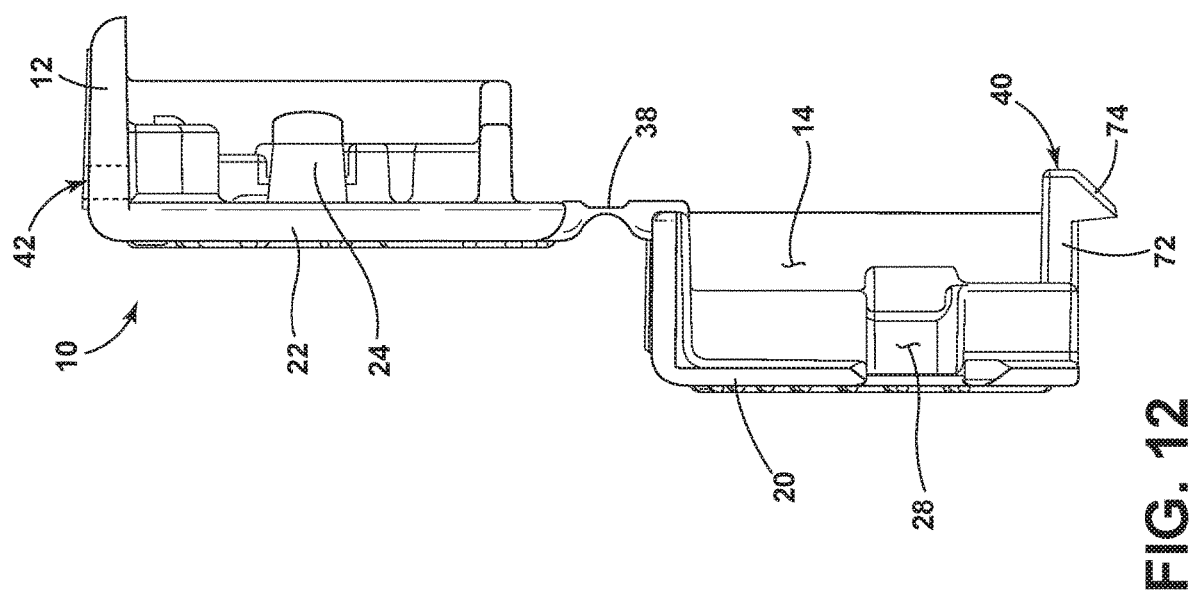
FIG. 12 is a rear elevational view of the blade loader having a housing with a first section hingedly coupled to a second section, according to some examples.

Referring to FIG. 5, the insertion opening 16 may be disposed at one end portion of the cavity 14. As provided herein, the blade 18 is retained within the cavity 14 and maintains a clearance from the sidewalls of the housing 12. The blade 18 may be maintained in a substantially fixed location through the support 24 and the pressing portion 32 on the first rib structure 28 (FIG. 12). The support 24 may extend from the second section 22 of the housing 12. In some examples, as illustrated in FIG. 6, the support 24 extending from the second section 22 may at least partially align with a slot 62 in the first section 20 of the housing 12.

Referring to FIGS. 3-10, the blade 18 may be a first distance $d_1$ from the first sidewall 34 disposed below the blade 18 and a second distance $d_2$ from a first top wall 76. Moreover, the cutting edge 60 of the blade 18 maintains a clearance between the interior surface of the first and second sidewalls 34, 36. As provided herein, the blade 18 maintains clearance from the walls through the usage of the first rib structure 28 having a press portion 32, one or more protrusions 66, 68, and/or locating features defined by the first rib structure 28.

Figure 6:
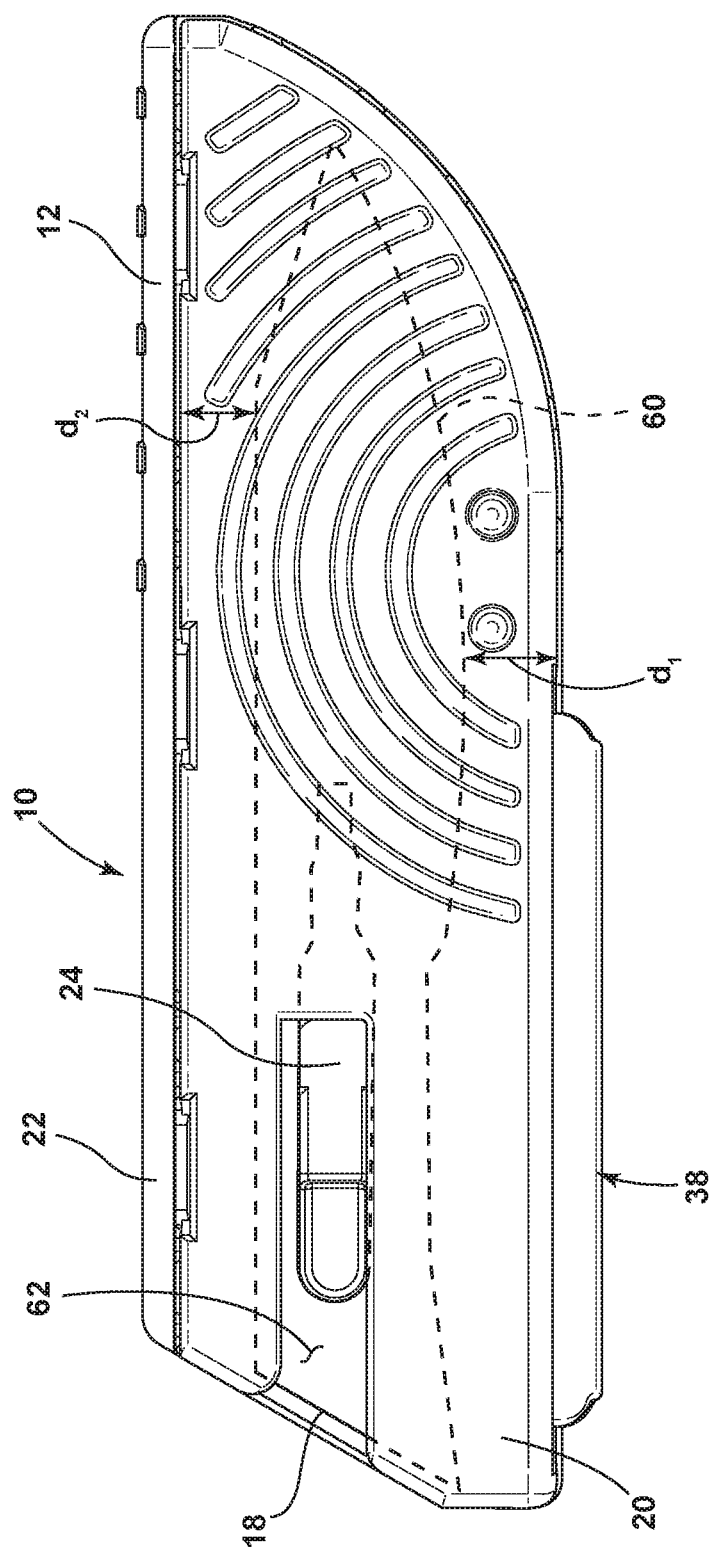
FIG. 6 is a first side elevational view of the blade loader, according to some examples.
Figure 7:
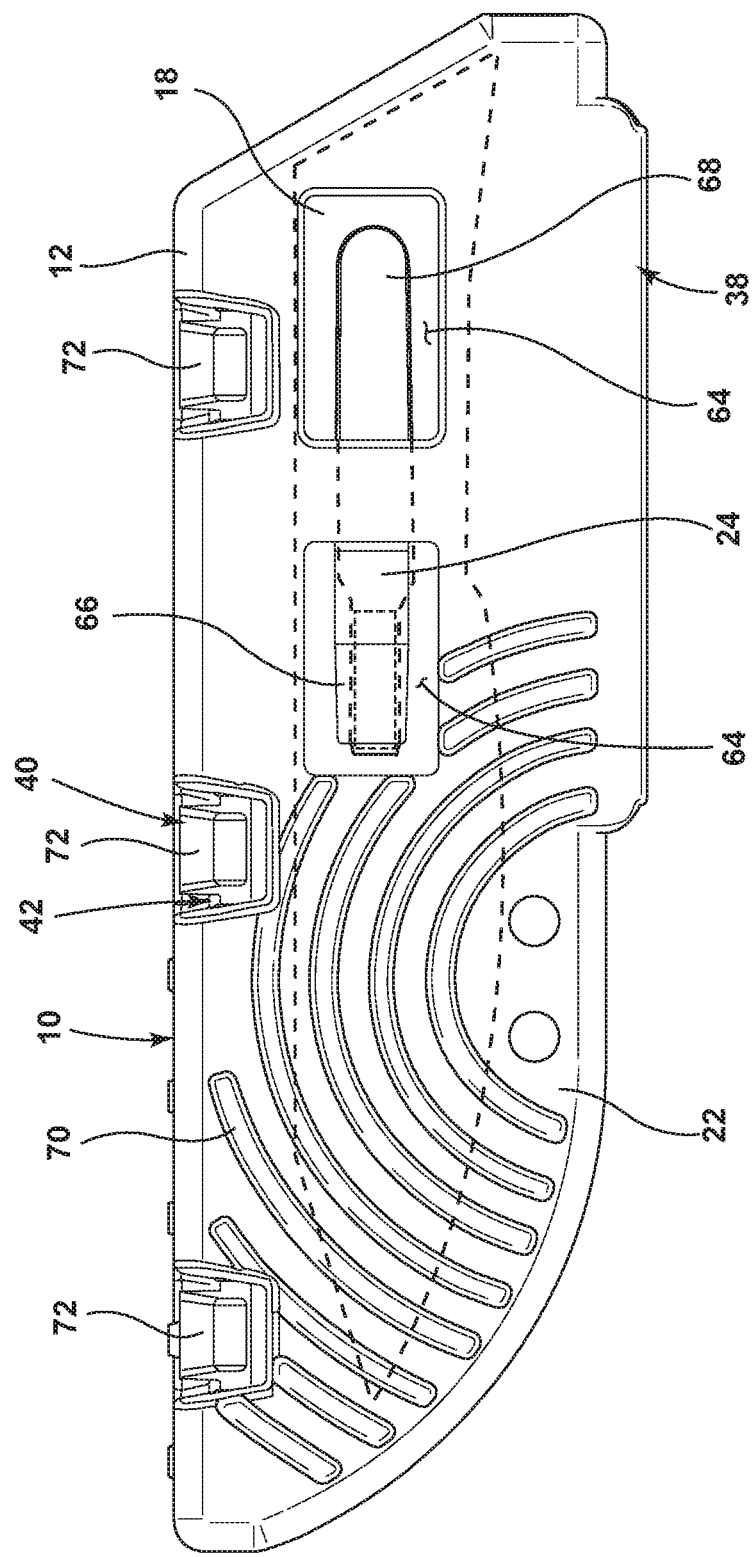
FIG. 7 is a second side elevational view of the blade loader, according to some examples.
Figure 8:
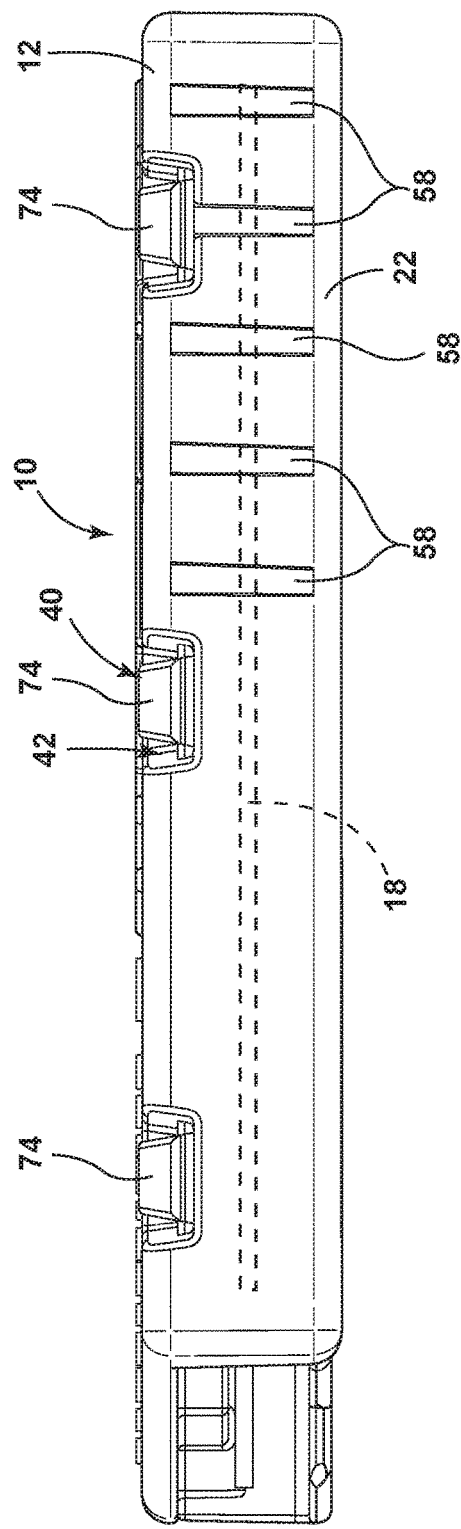
FIG. 8 is a top plan view of the blade loader, according to some examples.
Figure 9:
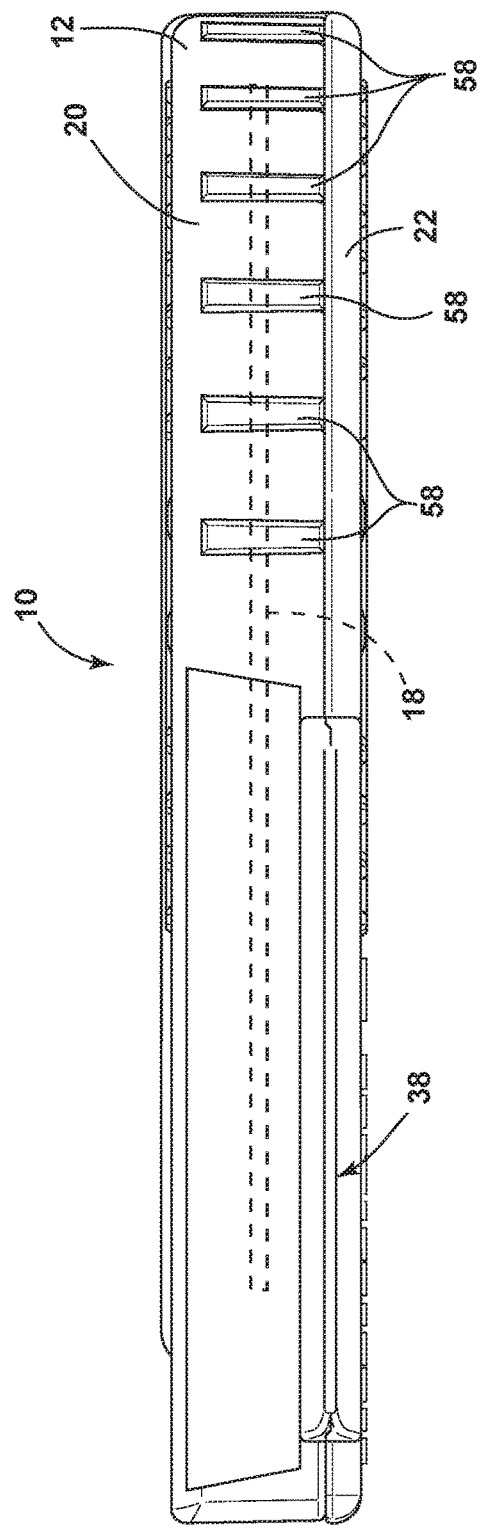
FIG. 9 is a bottom plan view of the blade loader, according to some examples.

Referring to FIGS. 6 and 7, the first section 20 defines the slot 62 therein. The slot 62 is configured to accept the tang 46 of the scalpel handle 48 therethrough for attachment of the blade 18 thereto. As will be described in greater detail below, the tang 46 may be inserted into the cavity 14 at an angle that is offset from the blade 18. In some examples, the support 24 extends from the second section 22 and into the cavity 14. The support 24 is configured to interact with an aperture 26 in the blade 18. A portion of the support 24 is disposed forwardly of an end portion of the slot 62.

Referring to FIG. 7, the second section 22 of the housing 12 includes the support 24 extending into the cavity 14. The second section 22 may define one or more holes 64 disposed on each side of the support 24. First and second protrusions 66, 68 may extend from the support 24 in opposing directions. The holes 64 may allow the first and second protrusions 66, 68 to be integrally formed with the support 24 during a manufacturing process, such as an injection molding process. It will be understood, however, that any manufacturing process may be utilized to form the housing 12. Accordingly, in some examples, the holes 64 may not be present on the second section 22 of the housing 12. The holes 64 may also allow for deflection of the first and second protrusions 66, 68 there into when the tang 46 is inserted into the aperture 26 defined by the blade 18.

Referring to FIGS. 6-10, the first and/or second sections 20, 22 of the housing 12 may include a grip feature 70. According to some examples, the grip feature 70 may include one or more corrugations extending from the first and/or second sections 20, 22. In some examples, the corrugations may be arcuate to define a desired area for a user to hold and/or compress the housing 12 while attaching the blade 18 to the scalpel handle 48. Accordingly, the grip feature 70 may be proximate the press portion 32 of the first section 20.

With further reference to FIGS. 6-10, the attachment structure 40 is coupled to, or integrally formed with, the first section 20 for removably attaching the first section 20 to the second section 22. As illustrated, the attachment structure 40 on the first section 20 including a first surface 72 extending in a first direction and a second surface 74 extending in an outwardly, substantially perpendicular direction. The attachment structure 40 engages the corresponding attachment region 42. As illustrated, the attachment region 42 is configured as a void through which the attachment structure 40 is inserted. In some examples, the voids may be undersized to increase the permanency of the closure. Thus, once the first section 20 is coupled to the second section 22, forming the cavity 14 therebetween, it may be difficult to separate the first section 20 from the second section 22.

Figure 10:
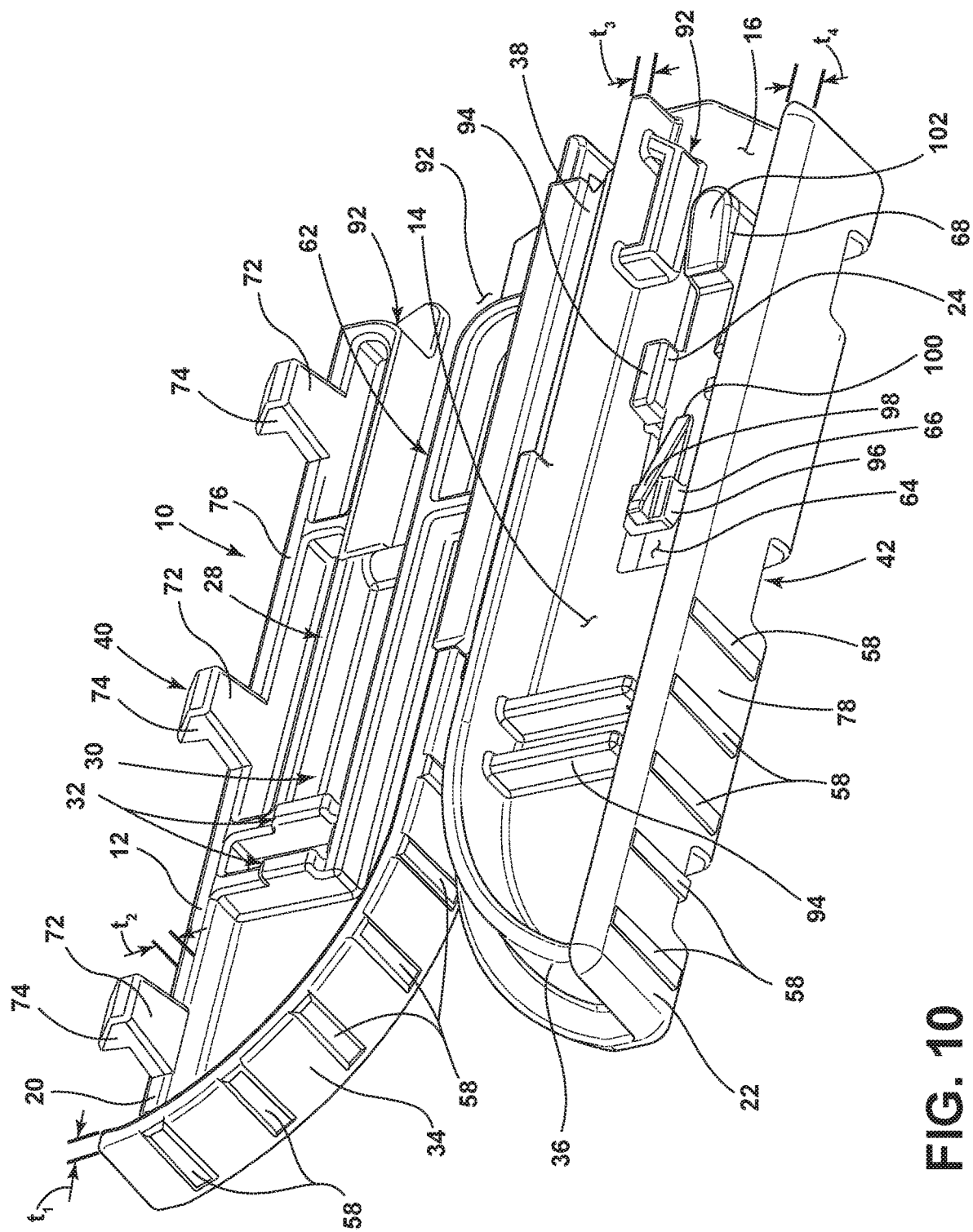
FIG. 10 is a top perspective view of a cavity of the blade loader, according to some examples.
Figure 11:
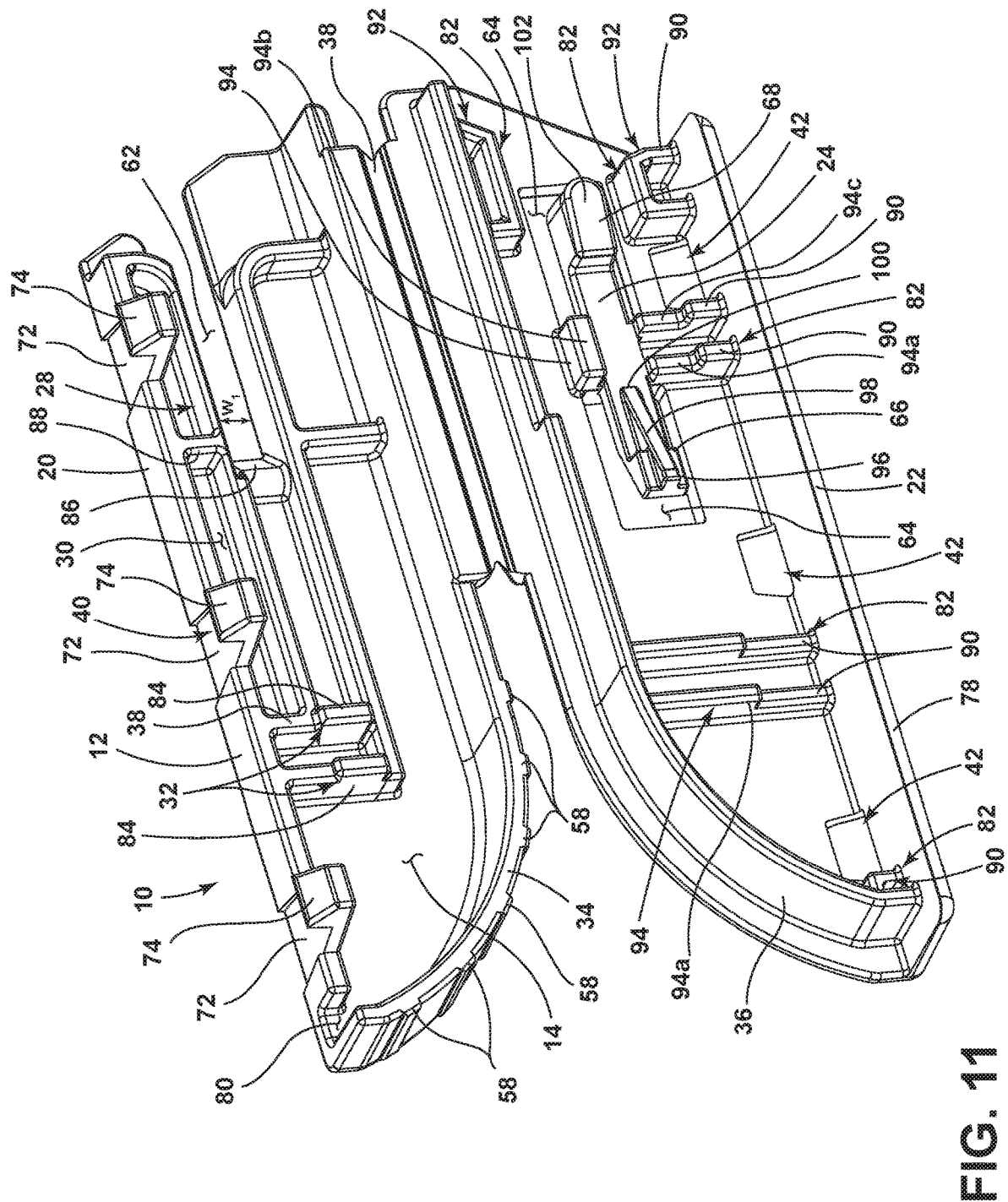
FIG. 11 is a bottom perspective view of a cavity defined by the blade loader, according to some examples.
Figure 13:
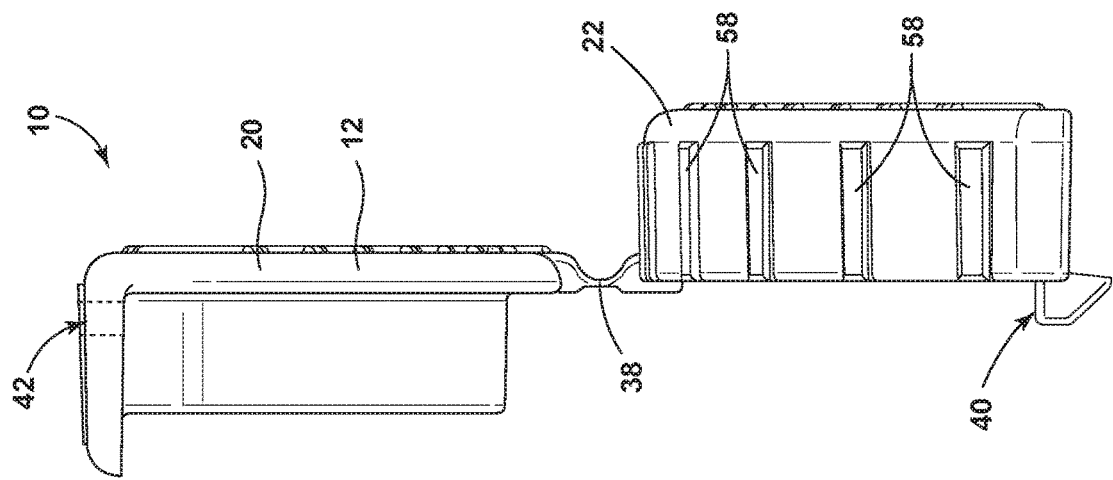
FIG. 13 is a front elevational view of the housing with the first section hingedly coupled to the second section, according to some examples.

Referring to FIGS. 10 and 11, the first section 20 of the housing 12 includes the first sidewall 34 and a first top wall 76. The second section 22 of the housing 12 includes a second sidewall 36 and a second top wall 78. As illustrated in FIG. 11, the first sidewall 34 may be separated from the first top wall 76 by a gap 80. Conversely, the second sidewall 36 may terminate at the second top wall 78. In some examples, the first sidewall 34 may be disposed outwardly of the second sidewall 36 while the second top wall 78 is disposed outwardly of the first top wall 76. In such instances, when the first section 20 is coupled to the second section 22, the second sidewall 36 may be disposed within the gap 80. Additionally, the attachment structure 40 of the first section 20 may be disposed inwardly of the attachment region 42 of the second section 22. In some examples, the overlapping of the first and second sidewalls 34, 36, and the first and second top walls 76, 78 creates an additional layer that the blade 18 would need to puncture to exit the housing 12 through a portion thereof other than the insertion opening 16.

With further reference to FIGS. 10 and 11, the first sidewall 34 has a first thickness $t_1$, the second sidewall 36 has a second thickness $t_2$, the first top wall 76 has a third thickness $t_3$ and the second top wall 78 has a fourth thickness $t_4$. In some examples, the first and second thicknesses $t_1, t_2$ may be substantially equal. Likewise, the third and fourth thicknesses $t_3, t_4$ may be substantially similar. In some examples, the first and/or second thicknesses $t_1, t_2$ may be larger than the third and/or fourth thicknesses $t_3, t_4$. In alternate examples, each thickness $t_1, t_2, t_3, t_4$ may vary from the other thicknesses $t_1, t_2, t_3, t_4$.

The first and second sections 20, 22 may each include first and second rib structures 28, 82, respectively. The first rib structure 28 may define the press portion 32 and/or the channel 30. The press portion 32 may have a segment 84 that extends further into the cavity 14 than the proximate portions of the first rib structure 28. According to some examples, the press portion 32 may be configured to contact the proximate cutting portion 52 of the blade 18. The press portion 32 may aid in holding the blade 18 in a substantially constant position until the blade 18 is engaged with the tang 46. The press portion 32 may also assist in maintaining the stability of the blade 18 within the housing 12 during transit.

The channel 30 may be defined by the first rib structure 28 and configured to accept the tang 46 of the scalpel handle 48 therein. Accordingly, the channel 30 may have a width $w_1$ that is larger than a width $w_2$ of the tang 46 of the handle 48. As the tang 46 is inserted into the slot 62 in the first section 20 of the housing 12, the tang 46 may contact a chamfered abutment 86 that is disposed at an entry portion of the channel 30. The chamfered abutment 86 assists in guiding the tang 46 into the channel 30. In some examples, the channel 30 is disposed in a parallel direction to the slot 62 of the blade 18. Moreover, the segment 84 of the first rib structure 28 forming the press portion 32 may additionally define an end portion of the channel 30. The channel 30 may also restrain the tang 46 and/or scalpel handle 48 to prevent the cutting edge 60 of the blade 18 from contacting the housing 12 during removal therefrom. In some examples, the channel 30 may close off once the blade 18 and tang 46 are engaged and removed from the housing 12 to discourage unsafe reusing of the blade loader 10.

With further reference to FIGS. 10 and 11, the first and second rib structures 28, 82 include respective standoff portions 88, 90. The standoff portions 88, 90, when the first section 20 is attached to the second section 22, are in close proximity with, or contact, one another 20, 22. Accordingly, the standoff portions 88, 90 may minimize compression between the first and second sections 20, 22 to maintain engagement between the first and second sections 20, 22.

Referring still to FIGS. 10 and 11, the first and second rib structures 28, 82 may further define a stop 92 extending inwardly into the cavity 14. In some examples, the stop 92 is configured to be geometrically similar to the shoulder portion 50 of the scalpel handle 48 such that the scalpel 44 is inhibited from further insertion into the cavity 14. Moreover, the stop 92 may prevent a user from pressing the scalpel handle 48 and/or the blade 18 through the first or second sidewalls 34, 36 through over insertion of the handle 48 into the cavity 14.

With further reference to FIGS. 10 and 11, the second rib structure 82 may further define one or more blade braces 94. The blade braces 94 may contact a side of the blade 18 and prevent the blade 18 for being offset from a desired position. According to some examples, a first brace 94a may be disposed forwardly of the support 24. Second and third braces 94b, 94c may be disposed on opposing sides of the support 24. Moreover, one or more of the braces 94a, 94b, 94c, such as the third brace 94c, and the stops 92 may contact a back portion of the blade 18 to assist in vertical alignment of the blade 18 within the cavity 14.

Still referring to FIGS. 10 and 11, the support 24 includes a pair of cantilevered, or pivotable, first and second protrusions 66, 68 extending in opposing directions therefrom. As illustrated in FIG. 11, the first protrusion 66 may have a lower first portion 96 and a tapered centrally disposed second portion 98. As the scalpel tang 46 is slid into the cavity 14, the tang 46 may contact a base portion 100 of the second portion 98. As the tang 46 slides along the first protrusion 66, the first protrusion 66 is pushed towards the second section 22 of the housing 12 and out of the aperture 26 defined by the blade 18.

The second protrusion 68 extends in opposing direction from the first protrusion 66 and includes a tapered top surface 102. As illustrated in FIG. 11, in some examples, the tapered top surface 102 of the second protrusion 68 may have a thinner portion proximate the first protrusion 66 and a wider portion proximate the insertion opening 16. In some examples, the first or second protrusions 66, 68 may be pivoted within and/or through the holes 64 when the blade 18 is attached to the tang 46. Accordingly, in some examples, the first or second protrusion 66, 68 may be disposed outward of a portion of the second section 22 when pivoted away from the blade 18.

Referring to FIGS. 12-18, a method for attaching the blade 18 within the blade loader 10 to the scalpel handle 48 is described according to one example. As provided herein, injection molding may form the housing 12; however, any other manufacturing process known in the art may be utilized to form the housing 12. According to some examples, the hinge 38 may be integrally formed with the housing 12. Once the housing 12 is formed, the blade 18 (FIG. 3) may be disposed within the housing 12 and the attachment structure 40 on the first section 20 may be operably coupled to an attachment region 42 on the second section 22 thereby placing the blade 18 within the cavity 14. In some examples, the first and sections 20, 22 may be configured as a clamshell design. A clamshell design may be a one-piece container consisting of two sections 20, 22 joined by the hinge 38, which allows the structure to come together to close. Clamshells can use a variety of means of closing or sealing. For example, tabs, snaps, or have a friction fit may be used. Alternatively, adhesives, pressure-sensitive tapes, labels, staples, or are heat sealed materials may be utilized.

Figure 14:
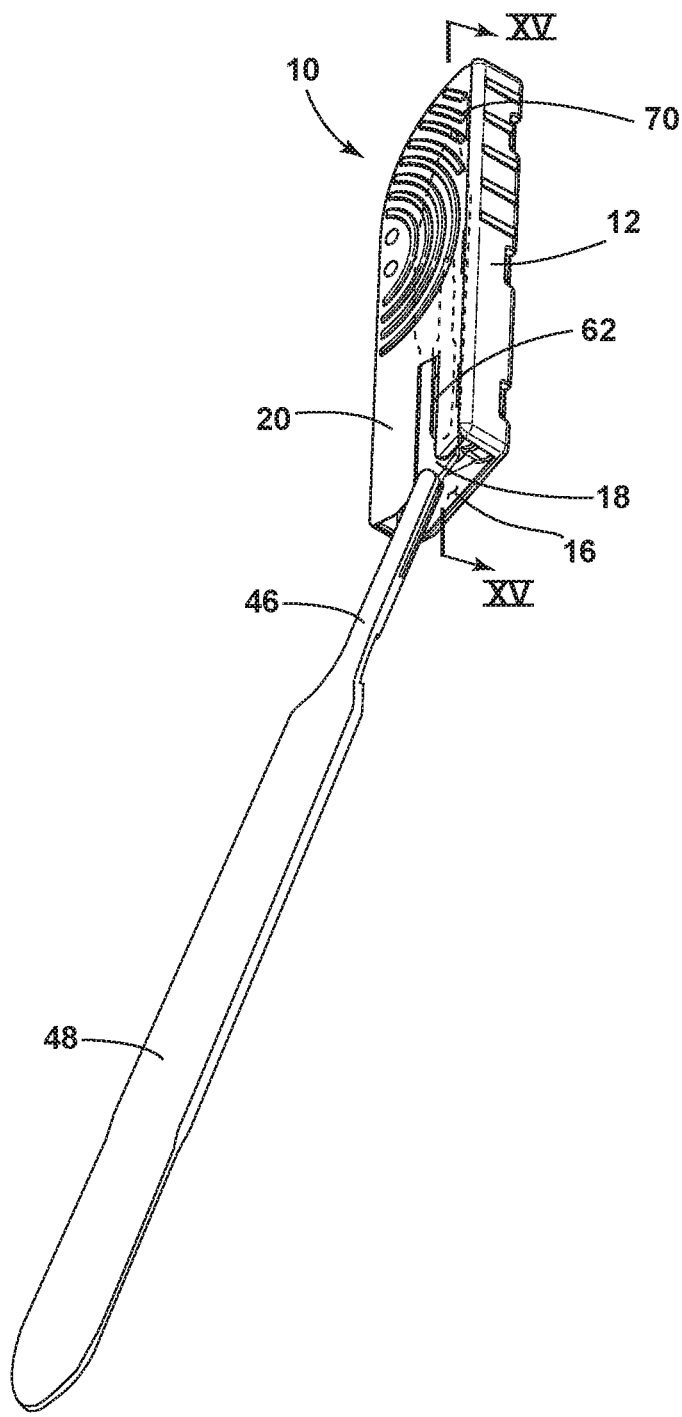
FIG. 14 is a side perspective view of the scalpel handle and the blade loader, according to some examples.
Figure 15:
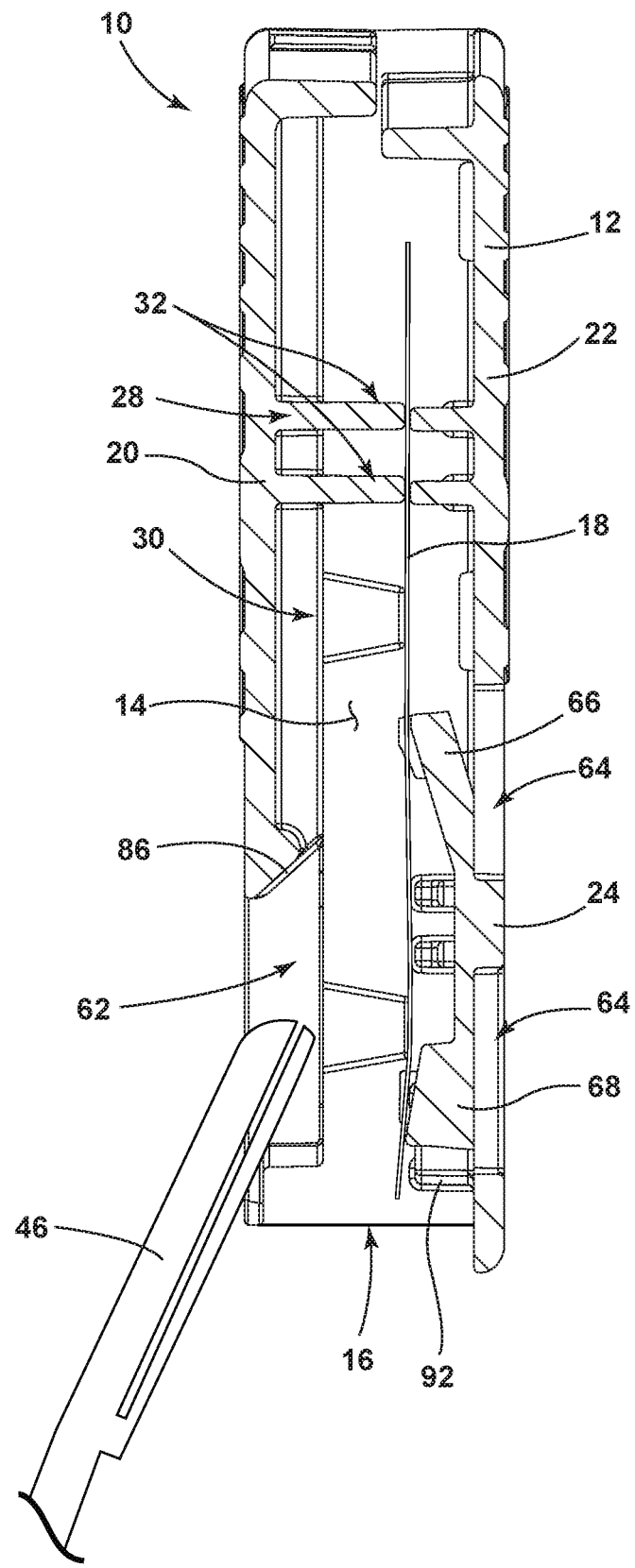
FIG. 15 is a cross-sectional view of the blade loader and a scalpel tang, according to some examples, taken along line XV-XV of FIG. 14.

Referring to FIGS. 14 and 15, once the blade loader 10 is to be used, the scalpel handle 48 is inserted into the cavity 14 through the slot 62 defined by the first section 20 of the housing 12 until the scalpel 44 contacts one or more stops 92. While the tang 46 is inserted through the slot 62 and insertion opening 16, the tang 46 of the scalpel handle 48 is guided within the channel 30. As the tang 46 is slid through the channel 30, a top portion of the tang 46 may slide along the tapered second portion 98 of the first protrusion 66 thereby pushing the first protrusion 66 out from the aperture 26 of the blade 18 as the tang 46 slides into the aperture 26. As the tang 46 is disposed within the cavity 14, the first and second protrusions 66, 68 are pressed out of the aperture 26 defined by the blade 18.

Figure 16:
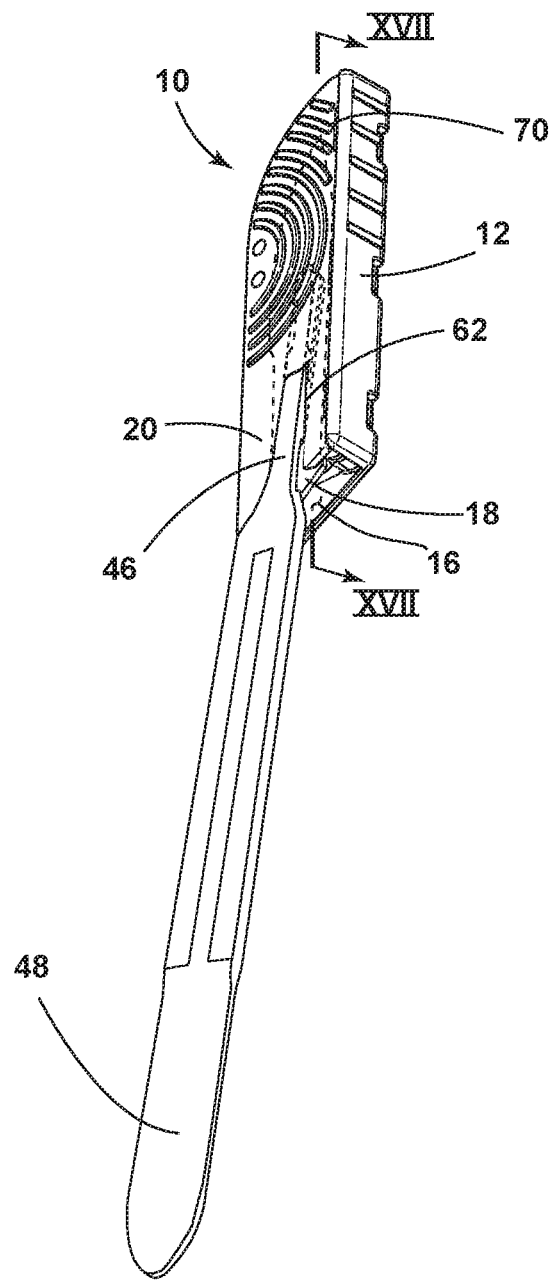
FIG. 16 is a side perspective view of the scalpel handle and the blade loader, according to some examples, with the tang of the scalpel handle disposed within the blade loader.
Figure 17:
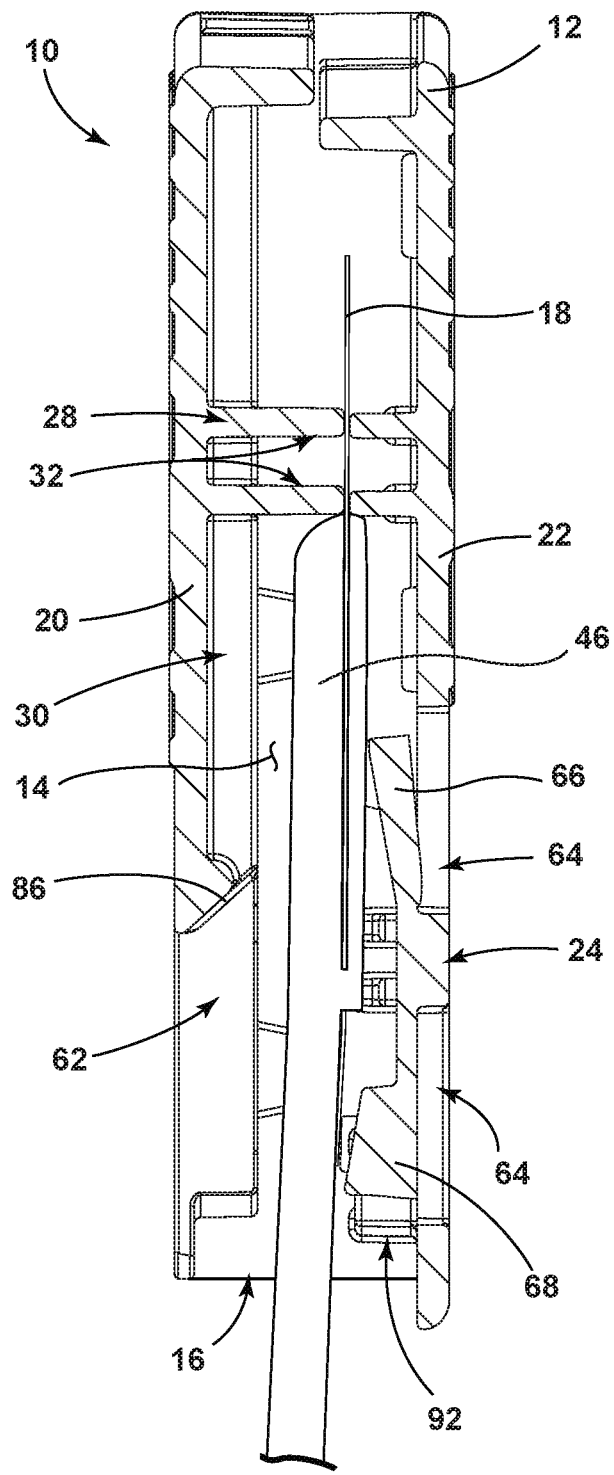
FIG. 17 is a cross-sectional view of the blade loader and the scalpel tang, according to some examples, taken along line XVII-XVII of FIG. 16.

Referring to FIGS. 16 and 17, the handle 48 may then move towards the second section 22 of the housing 12 in which the tang 46 may press the second protrusion 68 away from the blade 18 and onto the tang 46 thereby attaching the blade 18 to the tang 46. In some examples, the blade 18 may bend slightly away from the second protrusion 68, as the blade 18 is disposed on the tang 46. As provided herein, the protrusions 66, 68 may be disposed through the holes 64 as the tang 46 is coupled to the blade 18.

As provided herein, the housing 12 includes the first and/or second rib structures 28, 82 having a press portion 32 configured to maintain the blade 18 in a substantially fixed position as the scalpel 44 is inserted into the cavity 14. To inhibit insertion of the tang 46 past a desired position, the stops 92 may contact the shoulder portion 50 of the scalpel handle 48. Accordingly, once the shoulder portion 50 of the scalpel handle 48 contacts the stops 92, the blade 18 may be coupled to the tang 46.

Figure 18:
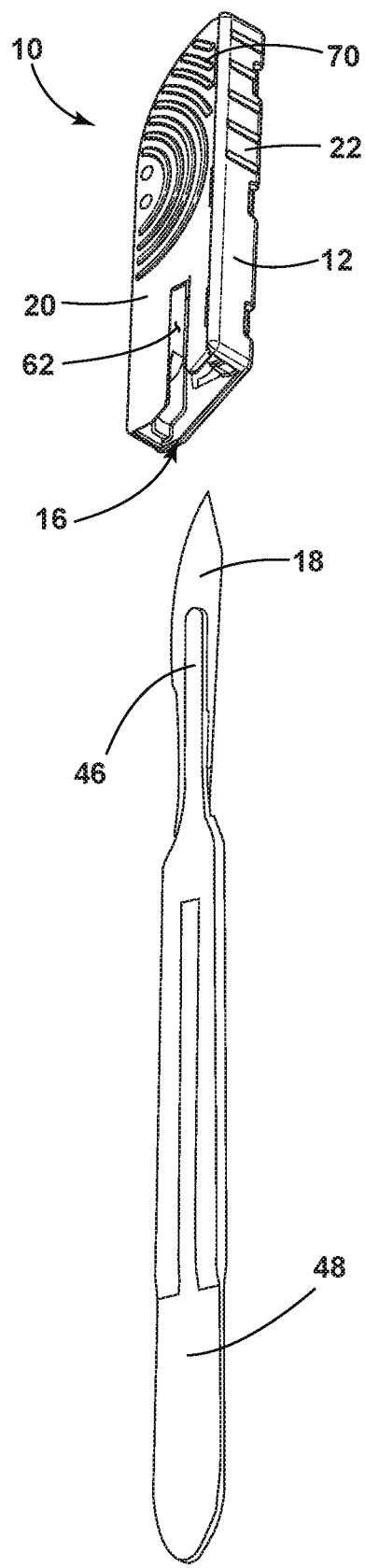
FIG. 18 is a side perspective view of the scalpel handle with the blade attached thereto, according to some examples.

Referring to FIG. 18, once the blade 18 is coupled to the tang 46, the scalpel handle 48 and the blade 18 may be removed from the cavity 14 through the insertion opening 16. In some examples, the tang 46 and the blade 18 may be removed from the cavity 14 with minimal resistive force. As discussed herein, as the blade 18 is removed from the cavity 14, the cutting portion 52 may be freely removed without contacting the housing 12.

Use of the blade loader provided herein allows for safer blade attachment leading to fewer punctures of health professionals while attaching the blade to the scalpel handle. The blade loader also assists in maintaining the sanitation of the cutting portion of the scalpel once the blade is attached to the scalpel handle. The blade loader may be interchangeably used with a wide range of scalpel handles. Furthermore, the blade loader may be manufactured at low costs when compared to various blade-holding devices known in the art.

It is also to be understood that variations and modifications can be made on the aforementioned structures and methods without departing from the concepts of the present device, and further it is to be understood that such concepts are intended to be covered by the following claims unless these claims by their language expressly state otherwise.

For purposes of this disclosure, the term "coupled" (in all of its forms, couple, coupling, coupled, etc.) generally means the joining of two components (electrical or mechanical) directly or indirectly to one another. Such joining may be stationary in nature or movable in nature. Such joining may be achieved with the two components (electrical or mechanical) and any additional intermediate members being integrally formed as a single unitary body with one another or with the two components. Such joining may be permanent in nature or may be removable or releasable in nature unless otherwise stated.

It is also important to note that the construction and arrangement of the elements of the disclosure as shown in the exemplary embodiments is illustrative only. Although only a few embodiments of the present innovations have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements shown as multiple parts may be integrally formed, the operation of the interfaces may be reversed or otherwise varied, the length or width of the structures and/or members or connectors or other elements of the system may be varied, the nature or number of adjustment positions provided between the elements may be varied. It should be noted that the elements and/or assemblies of the system might be constructed from any of a wide variety of materials that provide sufficient strength or durability, in any of a wide variety of colors, textures, and combinations. Accordingly, all such modifications are intended to be included within the scope of the present innovations. Other substitutions, modifications, changes, and omissions may be made in the design, operating conditions, and arrangement of the desired and other exemplary embodiments without departing from the spirit of the present innovations.

The above description is considered that of the illustrated embodiments only. Modifications of the device will occur to those skilled in the art and to those who make or use the device. Therefore, it is understood that the embodiments shown in the drawings and described above are merely for illustrative purposes and not intended to limit the scope of the device, which is defined by the following claims as interpreted according to the principles of patent law, including the Doctrine of Equivalents.

What is claimed is:

1. A blade loader, comprising:
   a housing defining a cavity and an insertion opening at one end portion of the cavity, the cavity configured to accept a blade therein, wherein the housing includes a first section coupled to a second section;
   first and second sidewalls extending from the respective first and second sections, the first sidewall disposed outwardly of the second sidewall;
   a support defined on the second section of the housing and including first and second cantilevered protrusions extending integrally with and in opposite directions along the second section of the housing from a central portion of the support that is integral with second section of the housing, each of the first and second cantilevered protrusions including respective portions extending inwardly into the cavity of the housing and configured to interact with an aperture in the blade; and
   a rib structure extending into the cavity and defining a channel and a press portion, the press portion configured to contact a portion of the blade.

2. The blade loader of claim 1, wherein the first section of the housing includes a slot therein, the slot configured to accept a tang therethrough.

3. The blade loader of claim 1, wherein the second section of the housing further defines respective first and second holes surrounding portions of the first and second cantilevered protrusions on opposite sides of the central portion of the support.

4. The blade loader of claim 3, wherein the first section includes a first top wall and the second section includes a second top wall.

5. The blade loader of claim 4, wherein the first top wall is disposed outwardly of the second top wall.

6. The blade loader of claim 5, wherein the first top wall includes an attachment structure thereon that is operably coupled to an attachment region of the second section.

7. The blade loader of claim 1, further comprising:
   a hinge operably coupling the first and second sections of the housing.

8. A blade loader, comprising: a housing including first and second sections defining a cavity therebetween and an insertion opening at one end portion of the cavity, the cavity configured to accept a blade therein, wherein the first section defines a slot proximate the insertion opening;
   and a support defined on the second section of the housing and including first and second cantilevered protrusions extending integrally with and in opposite directions along the second section of the housing from a central portion of the support that is integral with the second section of the housing, each of the first and second cantilevered protrusions including respective portions extending inwardly into the cavity of the housing and configured to interact with an aperture defined by the blade, wherein a portion of the support is disposed forwardly of an end portion of the slot.

9. The blade loader of claim 8, further comprising:
   a rib structure extending into the cavity and defining a channel, the channel having a width greater than a width of a tang of a scalpel handle.

10. The blade loader of claim 8, further comprising:
    a rib structure defined on both the first and second sections of the housing, extending into the cavity and defining a press portion and positioned away from the insertion opening past the support, the press portion configured to maintain the blade in a desired position.

11. The blade loader of claim 8, wherein the first section defines an attachment structure thereon that is operably coupled to an attachment region of the second section.

12. The blade loader of claim 8, further comprising:
    a hinge coupling the first and second sections of the housing.

13. The blade loader of claim 8, wherein the first section defines a first sidewall and the second section defines a second sidewall, wherein a clearance is maintained between the blade and the first and second sidewalls as the blade is attached to a scalpel handle.

14. A blade loader, comprising: a housing defining a cavity and an insertion opening at one end portion of the cavity, wherein the housing includes a first section coupled to a second section;
    a blade disposed within the cavity;
    a rib structure extending into the cavity and configured to contact a portion of the blade;
    and a support defined on the second section of the housing and including first and second cantilevered protrusions extending integrally with and in opposite directions along the second section of the housing from a central portion of the support that is integral with second section of the housing, each of the first and second cantilevered protrusions including respective portions extending inwardly into the cavity of the housing and configured to interact with an aperture in the blade.

15. The blade loader of claim 14, wherein the first section of the housing includes a slot therein, the slot configured to accept a tang of a scalpel handle therethrough.

16. The blade loader of claim 14, further comprising:
    a hinge operably coupling the first and second sections of the housing.

17. The blade loader of claim 15, wherein the housing includes a stop for inhibiting further insertion of the scalpel handle into the cavity.

18. The blade loader of claim 14, wherein the second section of the housing further defines respective first and second holes surrounding portions of the first and second cantilevered protrusions on opposite sides of the central portion of the support.

19. The blade loader of claim 14, further comprising:
    a grip feature including one or more corrugations extending from the housing.

* * * * *